(12) United States Patent
Pierotti

(10) Patent No.: US 7,182,460 B2
(45) Date of Patent: *Feb. 27, 2007

(54) RADICALLY SHAPED LENSES AND GOGGLE ASSEMBLIES AND GLASSES EMPLOYING SAME

(76) Inventor: Elizabeth M. Pierotti, 17 Connecticut Rd., Little Compton, RI (US) 02837

( * ) Notice: Subject to any disclaimer, the term of this patent is extended or adjusted under 35 U.S.C. 154(b) by 0 days.

This patent is subject to a terminal disclaimer.

(21) Appl. No.: 11/089,729

(22) Filed: Mar. 25, 2005

(65) Prior Publication Data

US 2005/0179858 A1    Aug. 18, 2005

Related U.S. Application Data

(60) Continuation of application No. 10/612,958, filed on Jul. 7, 2003, now Pat. No. 6,871,952, and a division of application No. 09/645,339, filed on Aug. 25, 2000, now Pat. No. 6,343,860.

(60) Provisional application No. 60/150,803, filed on Aug. 26, 1999.

(51) Int. Cl.
  *G02C 7/02*    (2006.01)
(52) U.S. Cl. ....................... 351/159; 351/157
(58) Field of Classification Search ................. 351/159, 351/41, 157, 177, 43, 176
See application file for complete search history.

(56) References Cited

U.S. PATENT DOCUMENTS

| | | |
|---|---|---|
| 2,088,262 A | 7/1937 | Grano |
| D156,289 S | 11/1949 | Stegeman |
| D183,415 S | 8/1958 | Armant |
| 3,040,616 A | 6/1962 | Simpson |
| 3,233,249 A | 2/1966 | Baratelli |
| 3,526,449 A | 9/1970 | Bolle et al. |
| 3,672,750 A | 6/1972 | Hagen |
| 4,447,914 A | 5/1984 | Jannard |
| 4,522,768 A | 6/1985 | Roscrow et al. |
| 4,676,610 A | 6/1987 | Barkan et al. |
| 4,761,069 A | 8/1988 | Troung et al. |
| 4,836,960 A | 6/1989 | Spector et al. |
| 4,838,675 A | 6/1989 | Barkan et al. |
| 4,921,205 A | 5/1990 | Drew, Jr. et al. |
| D311,197 S | 10/1990 | Jannard |
| D320,402 S | 10/1991 | Jannard et al. |
| D323,333 S | 1/1992 | Jannard et al. |

(Continued)

OTHER PUBLICATIONS

"Logo Paris"; Advertisement; Review of Optometry, Jun. 1988; p. 93.

(Continued)

*Primary Examiner*—Hung Xuan Dang
(74) *Attorney, Agent, or Firm*—Gordon & Jacobson, PC

(57) ABSTRACT

The present invention relates to spherical-shaped see through lenses used in eyewear. The lenses have a substantially constant thickness and a substantially constant radius of curvature of between 28–19 mm. The spherical lenses may be supported in a frame formed of either rigid or flexible material and attached to a strap assembly adaptable to be worn by the user. Optionally, each of the lenses may be supported by a flanged member and ventilation passages preferably extending through the frame and/or the lenses to allow air to circulate around the lenses.

18 Claims, 13 Drawing Sheets

U.S. PATENT DOCUMENTS

| | | |
|---|---|---|
| D324,394 S | 3/1992 | Jannard |
| D324,528 S | 3/1992 | Jannard |
| D325,040 S | 3/1992 | Jannard |
| 5,093,940 A | 3/1992 | Nishiyama |
| 5,094,520 A | 3/1992 | Reshef et al. |
| D328,468 S | 8/1992 | Jannard |
| D329,445 S | 9/1992 | Jannard |
| D330,035 S | 10/1992 | Jannard |
| D330,716 S | 11/1992 | Jannard |
| D330,903 S | 11/1992 | Jannard |
| D331,587 S | 12/1992 | Jannard et al. |
| D331,763 S | 12/1992 | Jannard |
| D333,145 S | 2/1993 | Jannard |
| D335,887 S | 5/1993 | Jannard |
| D336,908 S | 6/1993 | Jannard |
| 5,249,001 A | 9/1993 | Jannard |
| D342,534 S | 12/1993 | Jannard et al. |
| D342,959 S | 1/1994 | Jannard et al. |
| D343,182 S | 1/1994 | Jannard |
| D344,281 S | 2/1994 | Jannard et al. |
| D344,742 S | 3/1994 | Jannard |
| 5,313,671 A | 5/1994 | Flory |
| 5,359,371 A | 10/1994 | Nolan |
| D354,968 S | 1/1995 | Jannard |
| 5,387,949 A | 2/1995 | Tackles |
| D356,323 S | 3/1995 | Yee |
| D356,324 S | 3/1995 | Yee |
| D358,600 S | 5/1995 | Jannard |
| D358,829 S | 5/1995 | Jannard et al. |
| D359,302 S | 6/1995 | Yee et al. |
| D359,748 S | 6/1995 | Yee |
| D359,749 S | 6/1995 | Yee |
| D359,971 S | 7/1995 | Jannard |
| D365,357 S | 12/1995 | Jannard et al. |
| D365,591 S | 12/1995 | Jannard et al. |
| D368,921 S | 4/1996 | Yee et al. |
| D369,375 S | 4/1996 | Jannard et al. |
| 5,541,674 A | 7/1996 | Jannard |
| 5,550,599 A | 8/1996 | Jannard |
| D374,448 S | 10/1996 | Yee et al. |
| D376,162 S | 12/1996 | Yee et al. |
| D376,163 S | 12/1996 | Jannard et al. |
| D376,609 S | 12/1996 | Yee et al. |
| D377,365 S | 1/1997 | Conway |
| D377,498 S | 1/1997 | Jannard et al. |
| 5,604,547 A | 2/1997 | Davis et al. |
| 5,610,668 A | 3/1997 | Mage |
| 5,625,425 A | 4/1997 | Kranhouse |
| 5,638,145 A | 6/1997 | Jannard et al. |
| 5,648,832 A | 7/1997 | Houston et al. |
| D384,362 S | 9/1997 | Yee |
| D384,364 S | 9/1997 | Yee |
| D384,686 S | 10/1997 | Jannard et al. |
| D385,291 S | 10/1997 | Jannard et al. |
| 5,689,323 A | 11/1997 | Houston et al. |
| D388,816 S | 1/1998 | Jannard et al. |
| 5,708,489 A | 1/1998 | Jannard |
| 5,708,832 A | 1/1998 | Inniss et al. |
| D390,862 S | 2/1998 | Gallo |
| D392,662 S | 3/1998 | Jannard et al. |
| 5,730,155 A | 3/1998 | Allen |
| 5,732,415 A | 3/1998 | Boyd |
| 5,760,868 A | 6/1998 | Jannard et al. |
| 5,774,201 A | 6/1998 | Tackles |
| D397,131 S | 8/1998 | Yudis |
| D397,132 S | 8/1998 | Yee |
| D397,350 S | 8/1998 | Jannard et al. |
| D398,022 S | 9/1998 | Jannard et al. |
| D398,326 S | 9/1998 | Jannard et al. |
| 5,801,805 A | 9/1998 | Mage |
| 5,805,261 A | 9/1998 | Houston et al. |
| D399,239 S | 10/1998 | Jannard et al. |
| D399,240 S | 10/1998 | Jannard et al. |
| D399,243 S | 10/1998 | Jannard et al. |
| D399,519 S | 10/1998 | Yee |
| D399,865 S | 10/1998 | Jannard et al. |
| D399,866 S | 10/1998 | Yee |
| 5,827,583 A | 10/1998 | Ambler |
| D402,304 S | 12/1998 | Jannard et al. |
| D404,747 S | 1/1999 | Yee et al. |
| D404,754 S | 1/1999 | Yee et al. |
| D405,102 S | 2/1999 | Moritz et al. |
| 5,867,246 A | 2/1999 | Edwards et al. |
| D407,428 S | 3/1999 | Jannard et al. |
| D408,049 S | 4/1999 | Jannard et al. |
| D410,484 S | 6/1999 | Jannard et al. |
| D410,485 S | 6/1999 | Jannard et al. |
| 5,915,542 A | 6/1999 | Swiet |
| 6,142,624 A | 11/2000 | Morris et al. |
| 6,142,627 A | 11/2000 | Winthrop |
| 6,168,271 B1 | 1/2001 | Houston et al. |
| 6,260,967 B1 | 7/2001 | Edwards et al. |
| 6,305,800 B1 | 10/2001 | Miller et al. |
| 6,309,067 B1 | 10/2001 | Zeidler |
| 6,334,681 B1 | 1/2002 | Perrott et al. |
| 6,343,860 B1 * | 2/2002 | Pierotti ................. 351/159 |
| 6,361,166 B1 | 3/2002 | Perrott et al. |
| 6,364,481 B1 | 4/2002 | O'Conner et al. |
| D461,200 S | 8/2002 | Pierotti et al. |
| 6,440,335 B1 | 8/2002 | Kingsbury et al. |
| 6,454,408 B1 | 9/2002 | Morris et al. |
| 6,505,930 B1 | 1/2003 | Perrott et al. |
| 6,588,899 B2 * | 7/2003 | Pierotti ................. 351/159 |
| 6,871,952 B2 * | 3/2005 | Pierotti ................. 351/159 |

OTHER PUBLICATIONS

"The Eyeline Collection"; Rolaris; Advertisement, Optician Apr. 24, 1987 p. 27.

"U.S. Army Aeromedical Research Lab (USAARL) Report No. 91-13 (Mar. 1991)", cover and pp. 4-5; J. K. Crosley et al.

"U.S. Army Aeromedical Research lab (USAARL) Report No. 96-07 (Jan. 1996)", cover and p. 1137; R.M. Wildzunas.

"U.S. Army Aeromedical Research Lab (USAARL) Report No. 90-12 (May 1990)"; cover and p. 5; R. R. Levine et al.

Material at http://www.ilcdover.com/products/CBSysMasks/M43.htm and 2 photos.

Worldwide NBC Mask Handbook (Defense Technical Information Center, Alexandria, Virginia (Sep. 1992).

"U.S. Army Aeromedical Research Lab Report#LR-87-10-2-5; Aug. 1987"; Rash et al.

"Whatever your passion . . . " Flyer—.COPYRGT.2000/2001 by GreenHouse Grown Products, Inc.

* cited by examiner

Center of eye rotation and center of outer lens surface radius.

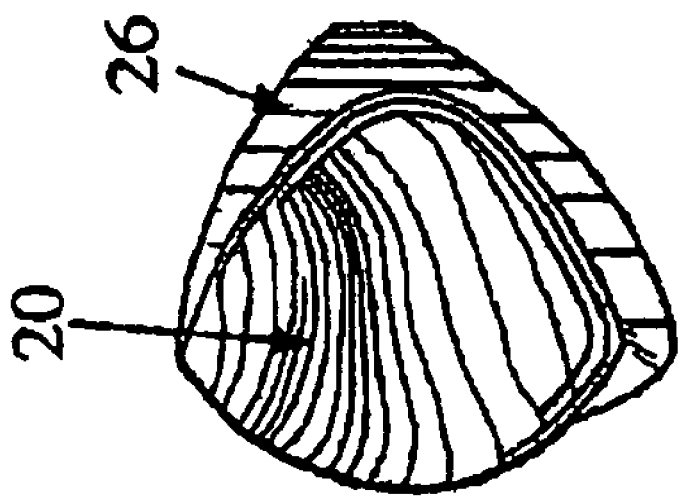
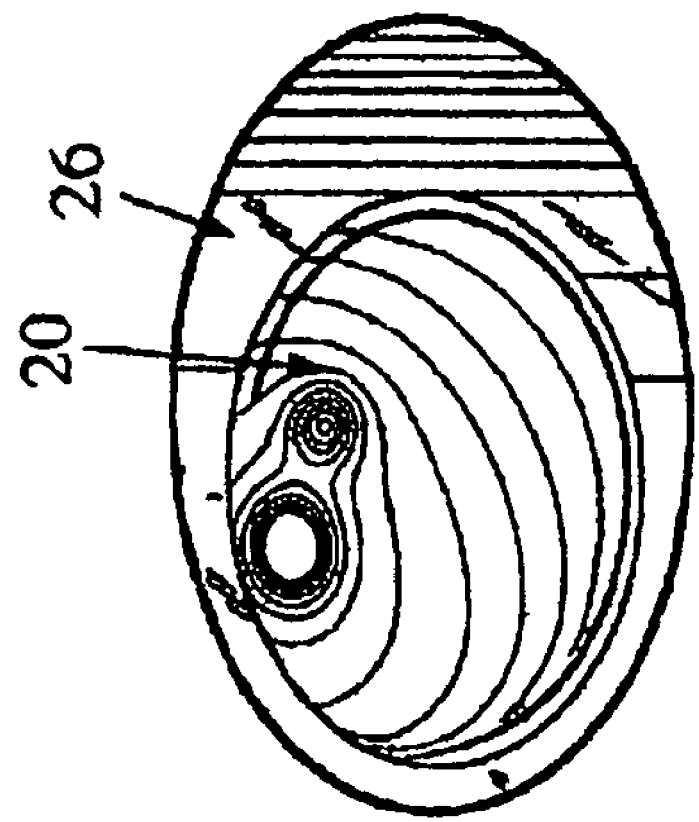
FIG. 3A
FIG. 3B

FIG. 3c
FIG. 3d
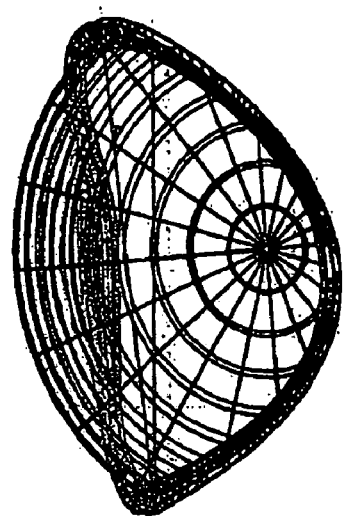
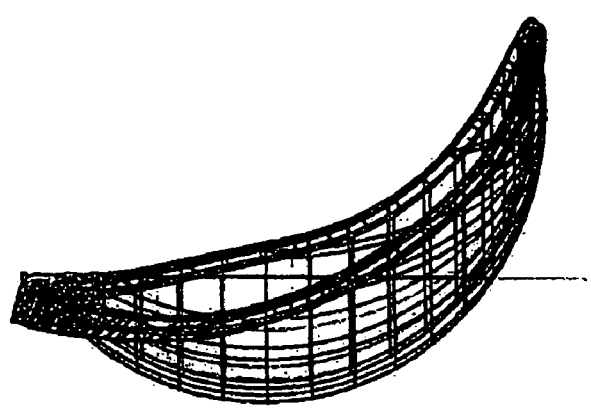

RADICALLY SHAPED LENSES AND GOGGLE ASSEMBLIES AND GLASSES EMPLOYING SAME

SUMMARY OF RELATED APPLICATIONS

This is a continuation of U.S. Ser. No. 10/612,958 filed on Jul. 7, 2003, now issued as U.S. Pat. No. 6,871,952 which was a division of application Ser. No. 09/645,339, which was filed on Aug. 25, 2000 and issued as U.S. Pat. No. 6,343,860 and claimed priority from provisional application 60/150,803 filed Aug. 26, 1999, all of which are hereby incorporated by reference herein in their entireties.

BACKGROUND OF THE INVENTION

The present invention relates to see-through lenses. More particularly, the present invention is directed to uniquely constructed, radically-shaped lenses, e.g., spheric or toric lenses having a radius-of-curvature between 28–19 mm (19–28 base curve), adaptable primarily for use in non-prescription sunglasses, sport goggles and the like, although not limited thereto.

As well as enhancing vision, eyeglasses also serve to protect the eye against all types of foreign objects. Initially, the lenses employed in such eyeglasses were routinely made of glass and were substantially flat in shape, a condition that created significant distortion around the periphery of the lenses. More recently, lenses have been made of a variety of plastic or plastic-like materials, often having dramatically curved surfaces. For example, swim or riding goggles are well know to have teardrop-shaped lenses. While such lenses may reduce aerodynamic drag, a wearer may suffer from undesirable peripheral distortion when viewing through such lenses.

Curved lenses employed in sports goggles, sunglasses or the like may be more or less elliptical in shape as required by the specific application. Such applications may include fashion eye wear, performance eyewear including swim and sport goggles, and sunglasses, as well as all manner of protective eye wear for use at home and on the job. In any particular use, the arc of the curved lens may vary in shape dependent on the overall circumference of the curved lens necessary to achieve undistorted vision. Lenses may be employed with a slight spherical appearance, i.e., a modified spherical, or ovoid arc. In such slightly curved lenses, there is a variable radius of curvature somewhere between 106–44 mm, e.g., a 5–12 base curve (base curve being calculated by dividing a radius in millimeters into 530). In effect, the distance between the lens and eye may well differ at different locations on the lens. This may create significant distortion at the periphery of each lens.

The Government of the United States has procured a protective facemask assembly having a pair of semi-curved lenses of spherical or ovoid configuration. While these lenses may seem superficially similar to the present invention, closer inspection reveals a number of significant differences. Because the Government lenses are mounted in pockets creating the nose bridge of the facemask, the edge of each Government lens is truncated or cut-off to allow for assembly into its respective pocket. This naturally creates peripheral distortion for the wearer of the mask, when attempting to view through the truncated portion located near the mask nose. Another drawback of the Government procured spherical lens is the use of only a single size lens, i.e. "one size fits all." Each Government lens also incorporates two parts, a spherical lens and surrounding flange joined by a dedicated and detectable seam. This seam itself can distort the vision of the wearer. Furthermore, there is no suggestion that the flange surrounding the Government's spherical lens can be made of any desirable configuration.

It is clear that there exists a need in the art for an improved viewing lens capable of providing distortion-free viewing in a fashionable design equally adaptable for use in most all types of eyewear including conventional, non-prescription sunglasses. As will become apparent, the present invention provides a uniquely configured lens assembly which optimizes peripheral vision while minimizing the size of each lens and thus maximizing the aerodynamic flow of air around the lens.

SUMMARY OF THE INVENTION

There is a need in the art for eyewear lenses capable of providing maximum field-of-view with a minimum of distortion. Such lenses need be adaptable for eyewear including sports wear and fashion wear. It is therefore an object of the present invention to provide such radically shaped lenses and associated eyewear.

It is another object of the invention to provide radically shaped lenses which provide increased sun, wind, and dust protection relative to the sunglasses and goggles of the art while at the same time improving central and peripheral vision with a lens that is in proximate relationship to the eye rotation at all times.

The present invention is directed to a radically shaped lens adaptable for use as a viewing lens in, e.g., protective eyewear, sunglasses, sport goggles, and swim wear utilized above the water. The invention includes a unique lens wherein the radius of curvature of the lens is substantially constant from a normal eyeball as it scans throughout the viewing field. Because the radius of curvature is substantially constant, the radically shaped, lens provides for continuous, undistorted peripheral vision. The radius of curvature of each radically shaped lens is preferably in the range of 28–19 mm, e.g., an exemplary lens with a base curve in the range of 19–28.

The lens of the invention is of substantially constant thickness throughout the field of view and the lens preferably only varies in thickness so that the lens can be is optically correct and free from any prism effect throughout the periphery of the lens and have a 0 power of magnification at all points in the viewing field when constructed of material having an index of refraction of between 1.55 and 1.66. A further feature of the present invention is that the closer the lens is positioned relative to the eye, the smaller in size the lens needs be. The lens is preferably no smaller than what is necessary to provide freedom of movement of the wearer's eyelashes. As the separation between the lens and the eye increases, the size of the lens will also increase, with the maximum practical size of the lens directly related to the facial geometry and to the point at which the wearer's eyes field of vision overlap.

A pair of the radically-shaped lenses according to the present invention may be directly attached to a pair of stems (also referred to as temples) extending about opposite sides of the wearer's head or attached to a goggle strap of any size and shape. Each radically shaped lens may include a flange portion (also called a "carrier") partially or totally surrounding the viewing lens. At the point where the lens and flange intersect, a seam may exist which visually differentiates between the lens and the flange. In one embodiment of the present invention, the lens and surrounding flange are separately constructed and joined at the seam. Alternatively, and more preferably, the lens and flange may be integrally constructed out of the same material with a gradual transition between the lens and flange portions providing a seamless appearance. The gradual transition may constitute a continuous and constant change of curvature, or may take any other desired shape. For example, the flange may contour to facial structure. Regardless of the type of construction employed, these flanges may serve to secure the lenses to a pair of eyeglass stems, padding, nose piece, ear piece, or strap, or the flange may be purely ornamental. The flange can be of any size, shape, color, texture, or material. It is also within the scope of the present invention to dispense with the flange altogether by directly connecting each radically shaped lens to the goggle or glass frame.

The percentage of the spherical lens which is used for the field-of-view should be sufficient to provide undistorted peripheral vision of at least 20° vertical and 20° horizontal and may be as great as 80° to 94° at the distal portion of each lens. As the proximal portion of the radically shaped lens, the nose would restrict overall monocular vision to field-of-view of about 140° to 156°.

BRIEF DESCRIPTION OF THE DRAWINGS

The various advantages of the present invention will become apparent to one skilled in the art by reading the following specification and by reference to the following drawings in which:

FIGS. 3a and 3b are front and side views, respectively, of a radically-shaped lens mounted in a flange and formed in accordance with the present invention while FIGS. 3c and 3d provide alternative views of the lens illustrated in FIGS. 3c and 3d;

DETAILED DESCRIPTION OF THE PREFERRED EMBODIMENTS

Figure 1A:
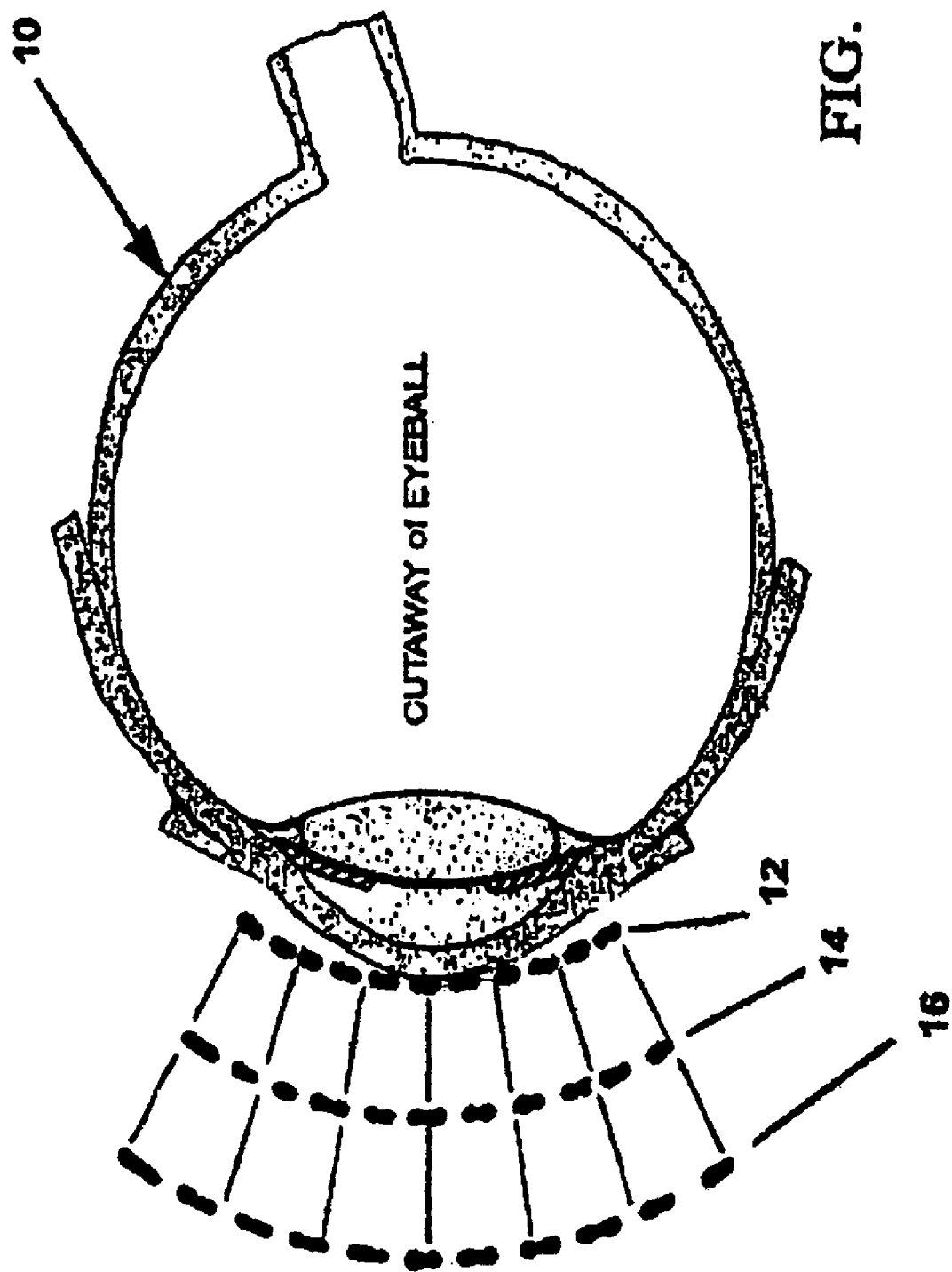
FIG. 1a is a cross-sectional view of an eyeball and two curved lenses formed in accordance with the present invention and FIG. 1b illustrates changes in the viewing angle when one of the lenses 14 or 16 is disposed proximate the user's eye.
Figure 1B:
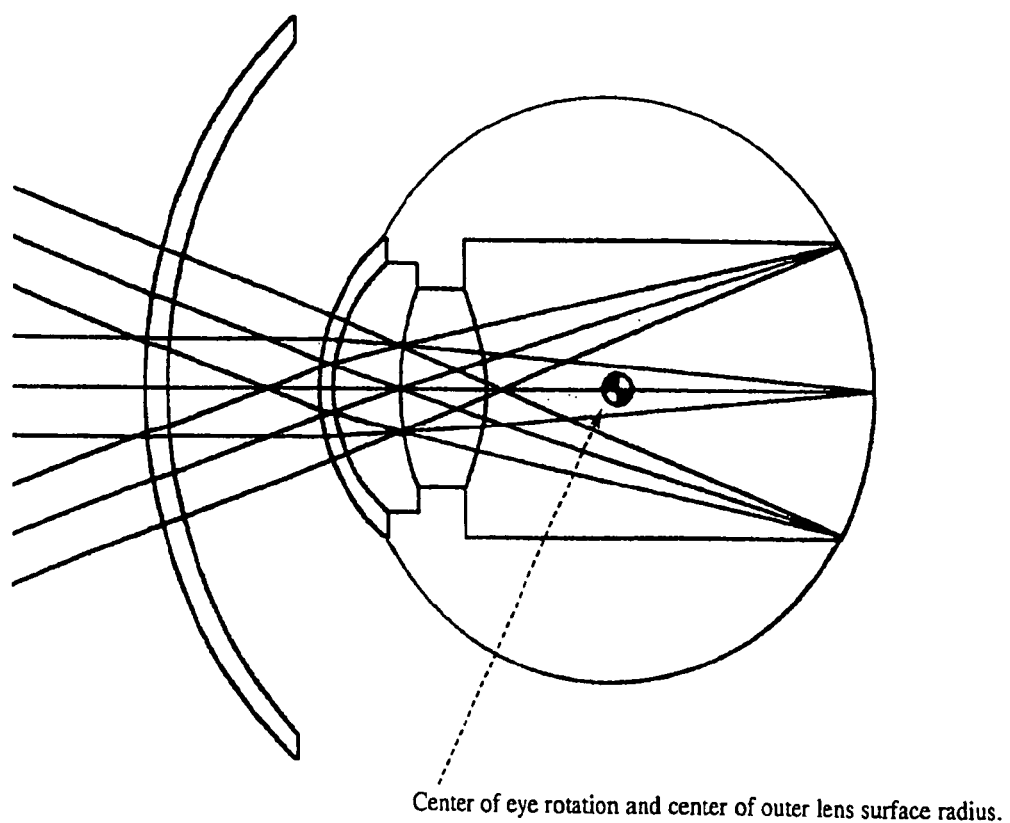
Figure 2B:
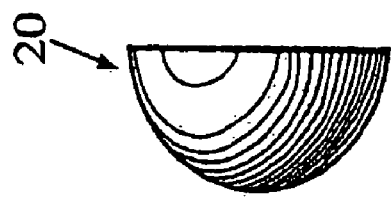
FIGS. 2a, 2b, 2c and 2d are face, side, top and back views, respectively, of a radically-shaped lens formed in accordance with the present invention.
Figure 2D:
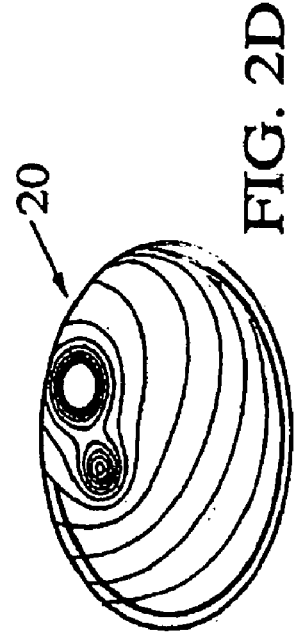
Figure 2A:
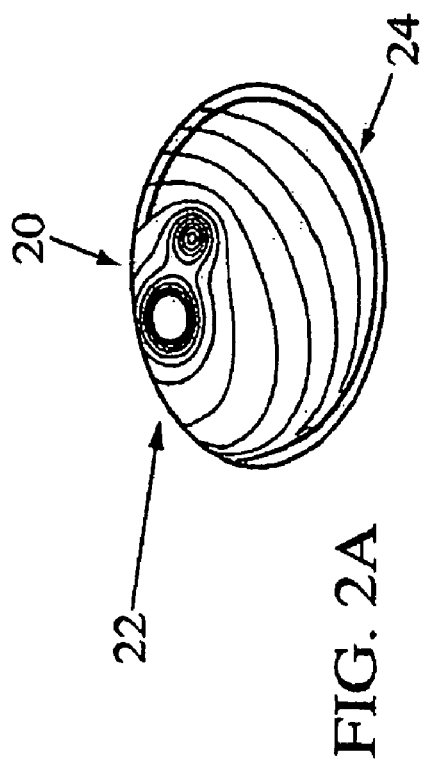
Figure 2C:
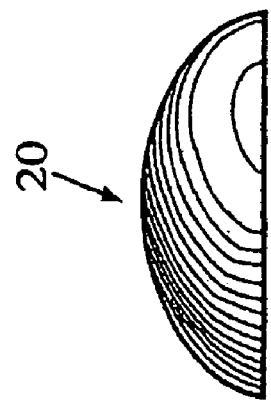

Illustrative embodiments and exemplary applications are described below with reference to the accompanying drawings in order to disclose the advantageous teachings of the present invention. Referring now to the drawings wherein like reference numerals designate like elements throughout, a typical eyeball is shown in cross-section in FIG. 1a at 10. The dotted line 12 traces the shape of the eyeball as it scans the field-of-view. The dotted lines 14 and 16 each show the shape of a radically shaped lens formed in accordance with the present invention. The lens 14 is at all times substantially equal distance from the line 12 delineating the eyeball 10. In a similar manner, the lens 16 is also at all times substantially equal distance from the line 12 of the eyeball 10. As will be understood, the lens 14 has a smaller radius of curvature than the lens 16. The difference in size between the lenses 14 and 16 results in a different field-of-view when scanned by eyeball 10. It will be appreciated that whether a spherical lens the size and shape of lens 14 or the size and shape of lens 16 is employed would depend on the desired field-of-view. FIG. 1b illustrates changes in the direction of view as the eye 10 rotates about its center relative to one of the lenses 14, 16.

Turning now to FIGS. 2a, 2b, 2c, 2d, wherein various views are shown of a radically-shaped lens 20 formed in accordance with the present invention. Lens 20 has a substantially constant radius of curvature, in the range of 28–19 mm. It will be appreciated that this radius of curvature is preferably constant with respect to all axes; although, if desired, the radius of curvature may be varied slightly along one axis. In addition, the thickness of spherical lens 20 is preferably constructed to be substantially constant throughout. More particularly, for non-prescription lenses the thickness of the lens varies preferably only to the extent necessary to permit the lens to be optically correct and free from any prism effect throughout the periphery of the lens and to have a 0 power of magnification at all points in the viewing field when constructed of material having an index of refraction of between 1.55 and 1.66. The percentage of the spherical shape of lens 20 used for viewing sufficient to provide undistorted peripheral vision of 20° vertical and 20° horizontal is between 80° and 94° at the distal portion 22 of the lens and between 140° and 156° at the proximal portion 24 of the lens.

Turning to FIGS. 3a and 3b, the radically shaped, e.g., spherical lens 20 includes a surrounding flange or carrier portion 26. Flange 26 joins and supports spherical lens 20 while providing points of attachment for connecting lens 20 to the frame portion of glass wear or goggles. Flange 26 may be formed of any convenient shape. As shown in FIG. 3b, flange 26 includes an elongated portion 28 located near the distal end of lens 20 remotely positioned from the adjacent lens as discussed below. FIGS. 3c and 3d provide alternative views of the lens 20. It is noted that flange portion may partially or totally surround the viewing lens. At the point where the lens and flange intersect, a seam may exist which visually differentiates between the lens and the flange. In one embodiment of the present invention, the lens and surrounding flange are separately constructed and joined at the seam. Alternatively, and more preferably, the lens and flange are integrally constructed out of the same material with a gradual transition between the lens and flange portions providing a seamless appearance. The gradual transition may constitute a continuous and constant change of curvature, or may take any other desired shape. For example, the flange may contour to facial structure. If desired, padding may be employed between the flange and the wearer's face. Regardless of the type of construction employed, these flanges may serve to secure the lenses to a pair of eyeglass stems, padding, nose piece, ear piece, or strap, or the flange may be purely ornamental. The flange can be of any size, shape, color, texture, or material. It is also within the scope of the present invention to dispense with the flange altogether by directly connecting each radically shaped lens to the goggle or glass frame.

Figure 4:
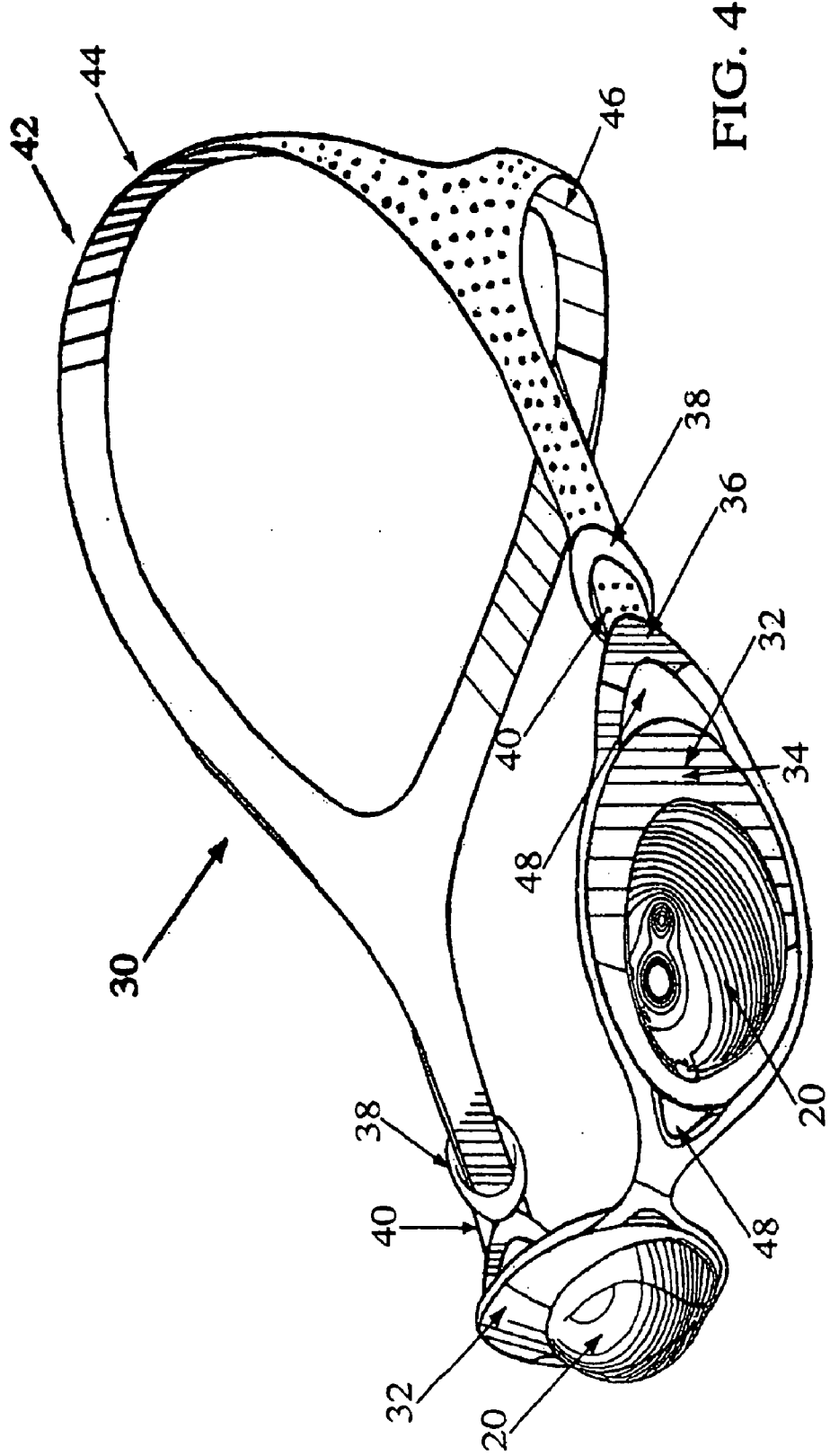
FIG. 4 is a perspective view of a performance goggle assembly formed in accordance with the present invention and including a pair of radically-shaped lenses formed in accordance with the embodiment of FIGS. 3a and 3b of the present invention.

Referring now to FIG. 4, a radical performance sport goggle assembly is generally indicated at 30. Goggles 30 include a pair of radically shaped lenses 20 each formed in accordance with the present invention. Each of the lenses 20 has a substantially constant radius of curvature in the range of between 28–19 mm. Each of the lenses 20 is mounted in a frame or holder 30. Holder 30 may be formed of a hard plastic material or, preferably, may be formed of soft, impact-resistant material. Holder 30 includes a pair of elongated eyepiece openings 34, with each opening 34 releasably retaining in place one lens 20. A particular retention assembly may comprise conventional clips, snaps, or other fasteners mounted on holder 30. When desired, each of the lenses 20 may be detached and replaced by different size lenses of the same or a different color. Holder 32 further includes end portions 36 with quick-release loop connector members 38 preferably formed of stretchable rubber, which may selectively enclose and retain opposite ends 40 of a strap 42 designed to extend around the wearer's head. By pulling the connector members 38 away from the wearer's face, it is possible to tighten the frame 30 and strap 42 about the wearer's head without forming any dangling ends. The strap 42 is preferably formed of sweat-absorbing material and may comprise a single band or two separate and yet connected band portions 44 and 46 which provide an ergonomic opening for secure and comfortable fit. As also shown in FIG. 4, a number of air flow/ventilation openings 48 are created between walls of each opening 34 and the radically shaped lenses 20. Because a considerable amount of air is allowed to move behind each of the lenses 20, they will not fog up as readily as conventional eyewear.

A particular benefit of the radically shaped lens 20 is its ability to be worn closer to the face than conventional eyewear. This is due to the radical radius of the lens 20. Even though the lens 20 closely fits over the wearer's eye, the eyelashes will have sufficient room to open and close without interference from the inside wall of the lens 20. Because the lens 20 is much closer to the eye then with conventional eyewear, there is a significant improvement of the peripheral vision. Such improved peripheral vision may provide the wearer with superior advance warning of potential danger at the periphery of the lens. Likewise, when a foreign object impacts the face, the fact that lens 20 is closer to the face because of its radically-shaped configuration, means that the distance that the impacted lens 20 moves is reduced, cushioning the blow to the face.

Figure 5:
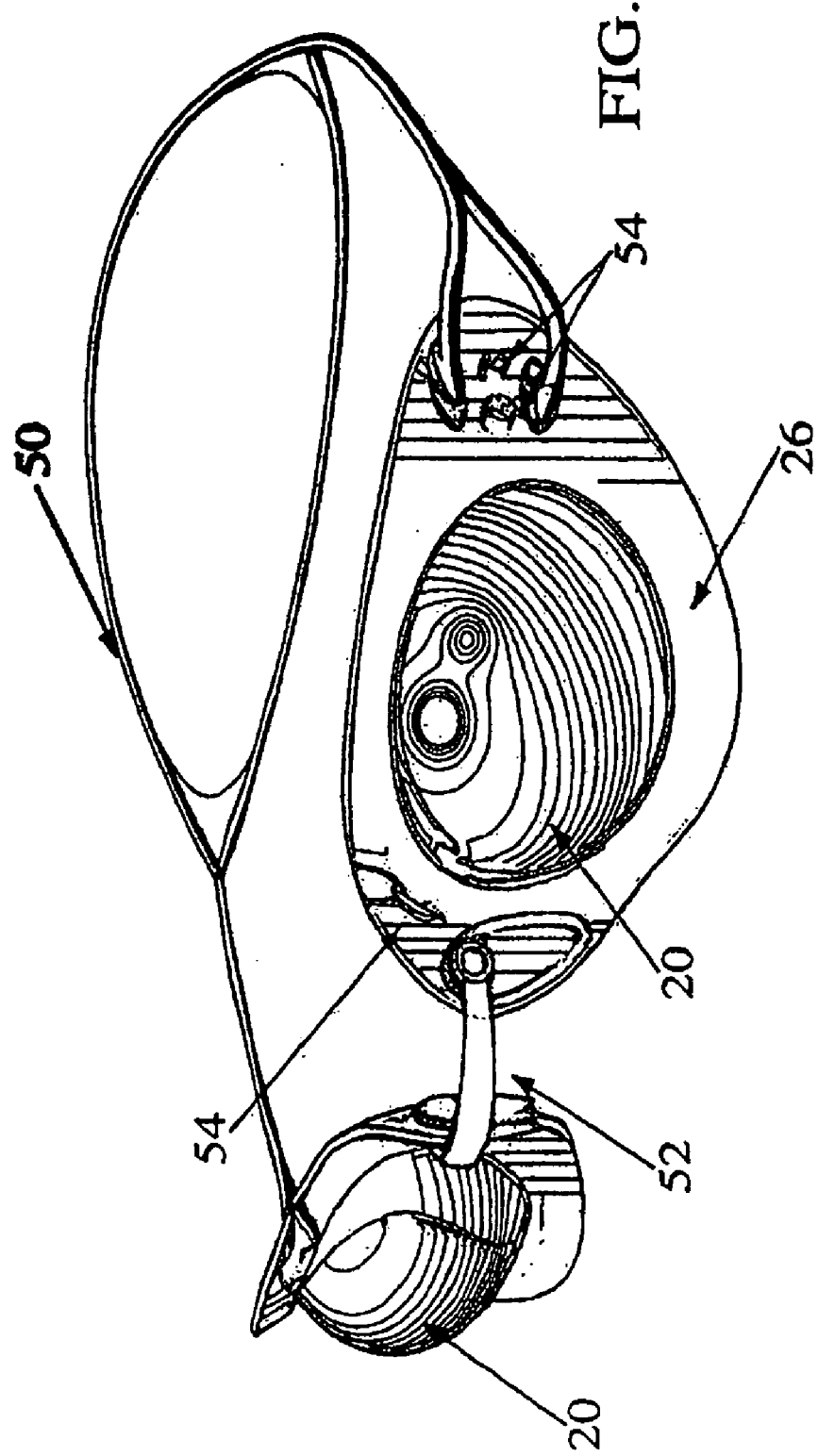
FIG. 5 is a perspective view of a further performance goggle assembly formed in accordance with the present invention and including a pair of radically-shaped lenses formed in accordance with the embodiment of FIGS. 3a and 3b of the present invention.

Instead of employing a frame or holder 34, the radically-shaped lenses 20 and surrounding flanges portions 26 may be directly attached to a strap 50 adaptable for encircling the wearer's head as shown in the embodiment of FIG. 5. A nose piece 52 joins the flanges 26 of the lenses 20 while a number of ventilation openings 54 extend though flanges 26 to allow air to freely circulate behind lenses 20.

Figure 6:
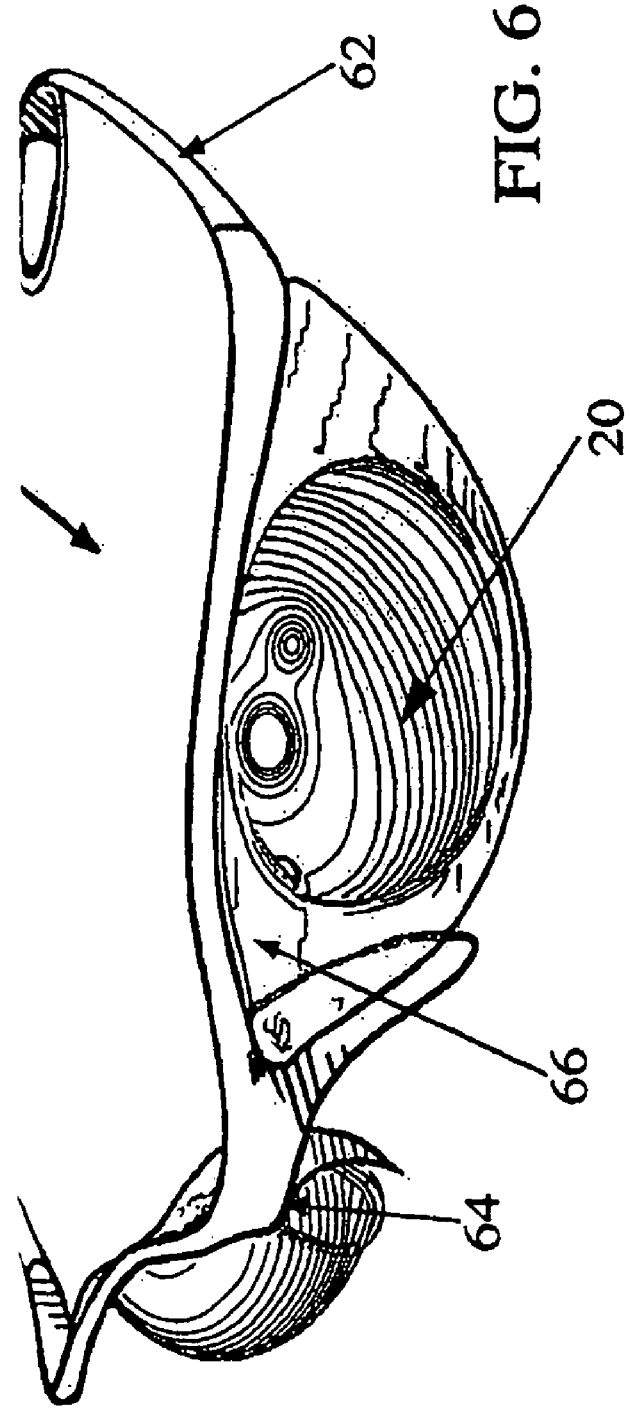
FIG. 6 is a perspective view of a pair of glasses formed in accordance with the present invention and including a pair of radically-shaped lenses formed in accordance with the present invention.

As shown in FIG. 6, a pair of lenses 20 and surrounding flanges 26 formed in accordance with the present invention are mounted in a frame assembly 60 formed of soft rubber or similar cushioning material. Frame 60 includes a pair of stems 62, which extend from the flanges 26 beyond the ears of the wearer, not shown. A nosepiece 64 supports a pair of adjacently disposed lenses 20. At least one elongated ventilation slot 66 extends between each of the spherical-shaped lenses 20 and the surrounding frame 60.

Figure 7:
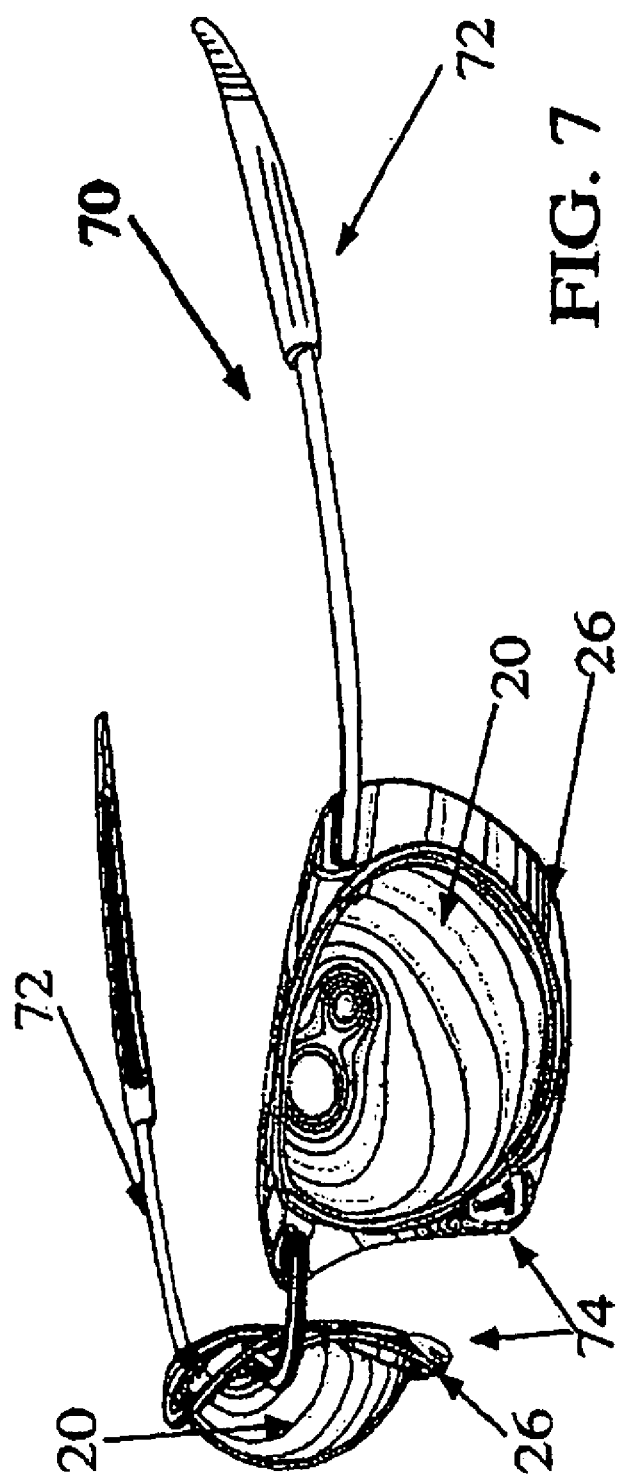
FIG. 7 is a perspective view of a further pair of glasses formed in accordance with the present invention and including a pair of radically-shaped lenses formed in accordance with the present invention.

In a further aspect of the present invention shown in FIG. 7, glasses 70 includes two lenses 20 each surrounded by a flange member 26. A pair of semi-rigid stems 72 are each connected to an outer portion of one of the flanges 26. A separate pad 74 is connected to the inner portion of each flange 26 with the pair of pads 74 serving to support the lenses 20 of glasses 70 on the bridge of the nose of the wearer, not shown. A connecting member 76 extends between flange members 26 and serves to join the lenses 20 together to form glasses 70.

Figure 8:
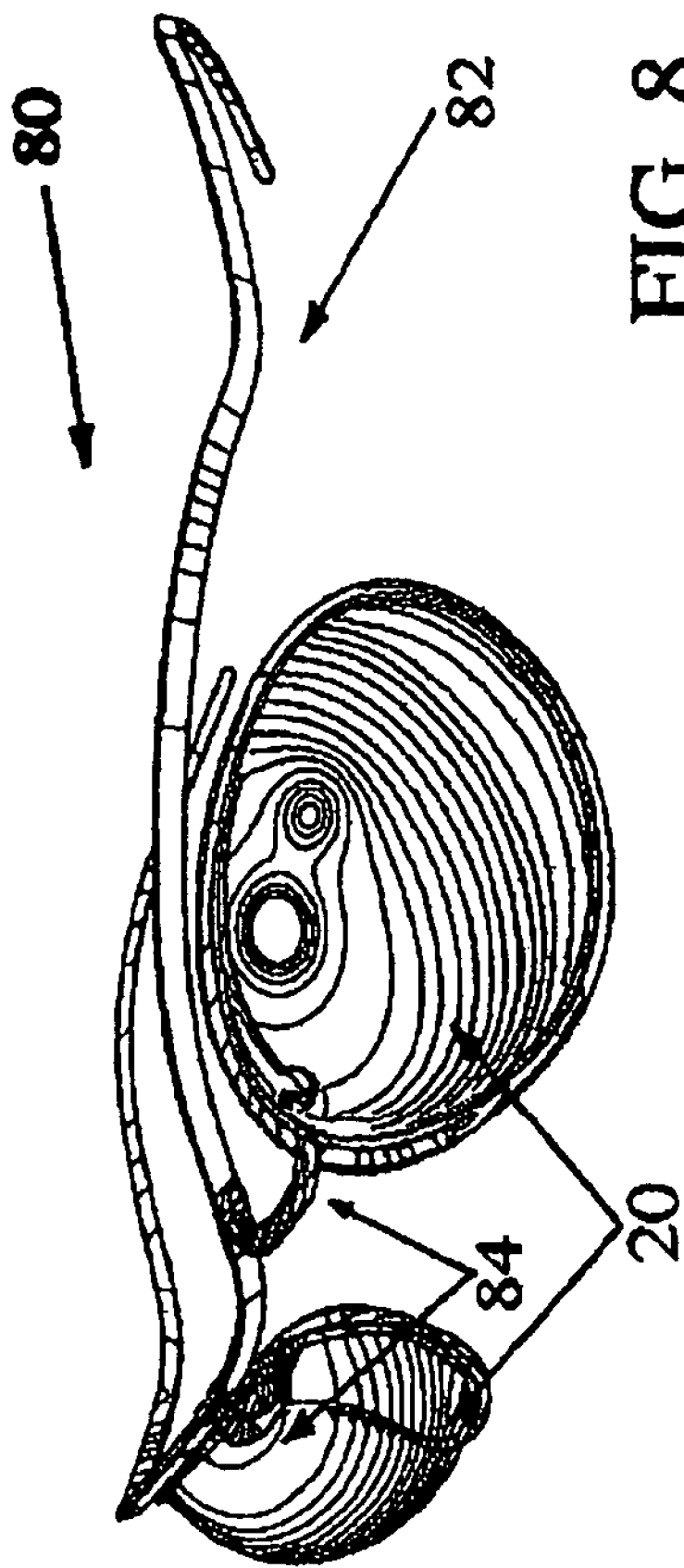
FIG. 8 is a perspective view of a further pair of glasses formed in accordance with the present invention and including a pair of radically-shaped lenses formed in accordance with the present invention.

In a yet further aspect of the present invention, the glasses 80 in FIG. 8 have eliminated the need for flanges 26. Rather, each of the pair of lenses 20 is directly connected to a frame 82 by at least one holder 84, which may comprise a wire or plastic member. It is also within the scope of the present invention for the lenses 20 to be directly connected to a pair of glass stems, a frame, paddings, and nose pieces in a manner similar to conventional lenses.

Figure 9A:
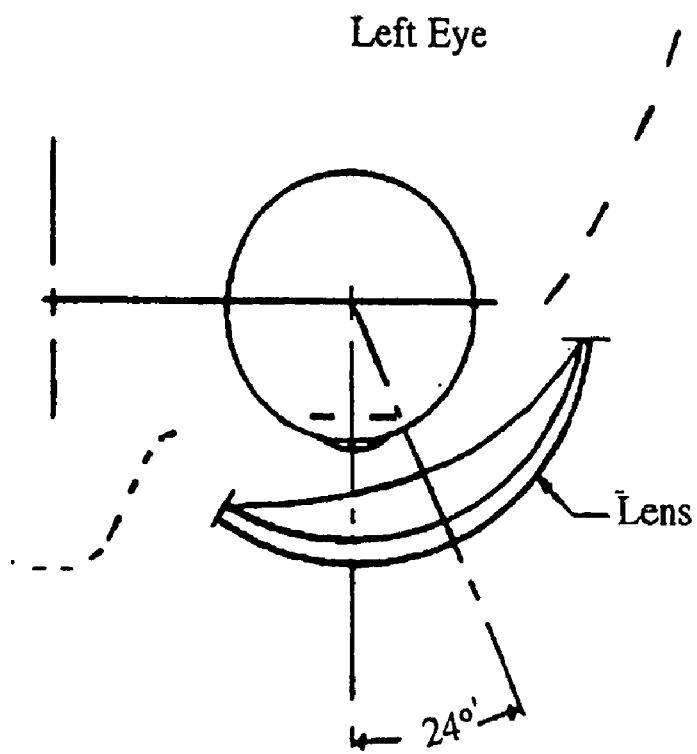
FIGS. 9a, 9b, and 9c provide additional information regarding the placement of the radically shaped lenses relative to the user's eye(s).
Figure 9B:
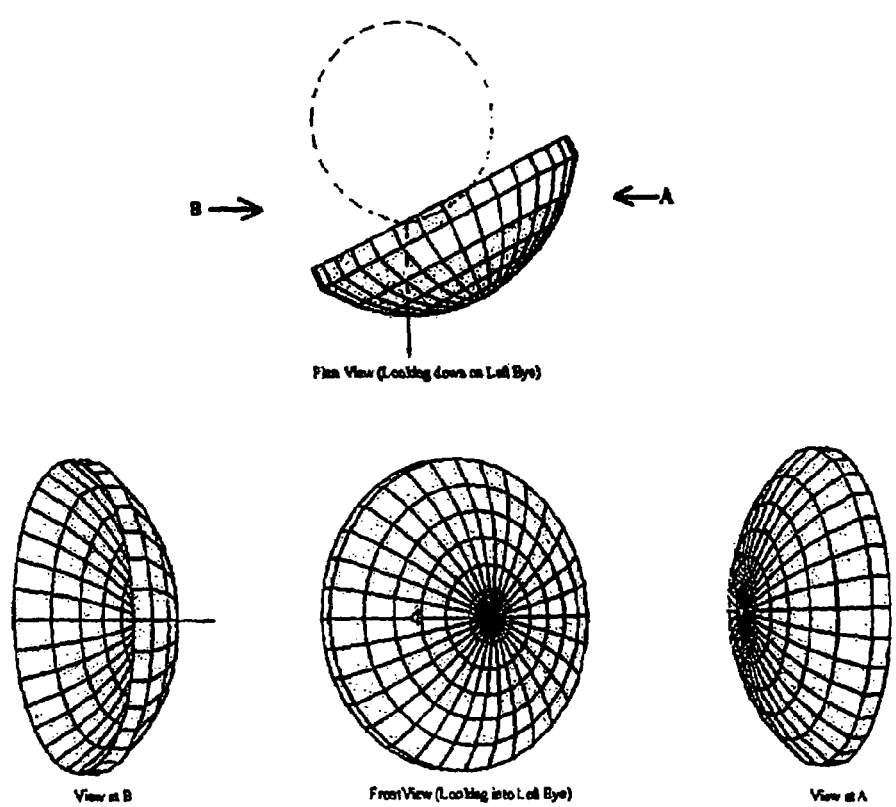
Figure 9C:
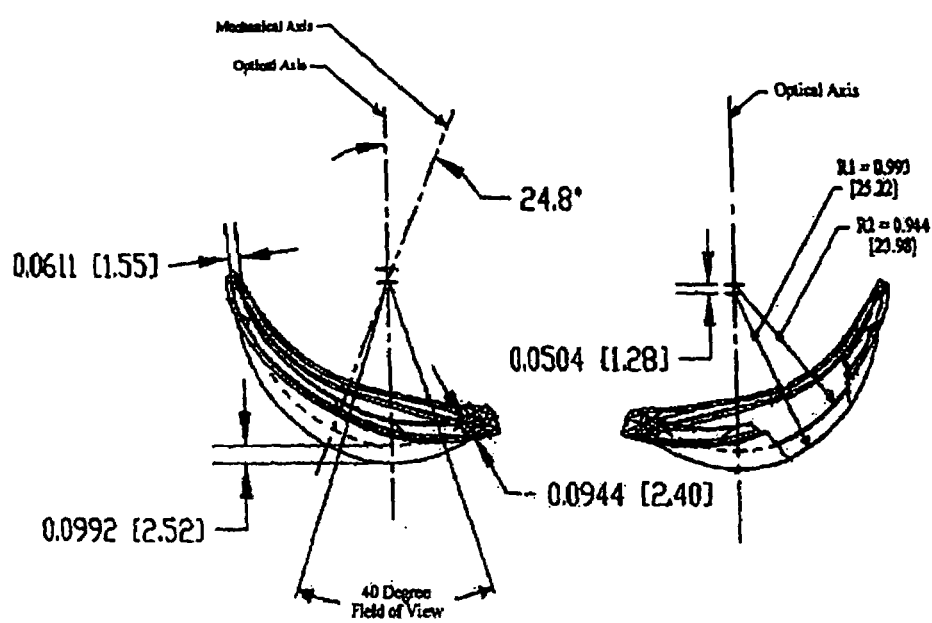

For each of the glasses or goggle assemblies formed in accordance with the present invention, the radically-shaped lenses 20 can be formed of smaller size and have an overall smaller footprint than achieved in known lenses. The lenses 20 need only surround the visible portion of the eyeball to function as effective eyewear, sunglasses or sport goggles. The overall spherical lens size is selected to meet the requirements of the particular sport or fashion application. This minimalistic approach particularly benefits speed related activities, sports, and even allows for a more even suntan. When used in sunglasses, the smaller size of the radically-shaped lens 20 offers more peripheral protection from UV rays than standard eyewear because the radically-shaped lens 20 almost entirely surrounds the exposed portion of the eyeball and can be worn much closer to the face than standard lenses. The overall advantages of the lens and goggles according to the present invention may best be understood from FIGS. 9a, 9b, and 9c, which provide views of the lens 20, or pair of lenses 20, disposed proximate to the user's eye(s).

The radically shaped lenses 20 exhibit a more aerodynamic in design when compared to traditional lenses. More importantly, lens 20 can be individually sized to fit the eye/facial area appropriate for wearers ranging from small children to large adults. It within the scope of the present invention to create lenses 20 in various sizes, colors, and materials sufficient to satisfy the vision requirements of almost any potential wearer.

The radically shaped lens 20 can be manufactured in any color, and may include any coating or design on the front of the lenses. Because the lens 20 does not have to be completely solid, a number of ventilation openings may extend through lens 20 to assist in airflow through the lenses. This will significantly benefit a user when subjected to heat, fog, or extreme weather conditions. The flange 26 surrounding lens 26 may be the same color as the lens 20 or a different color may be used to create two-toned eyewear. Glare resistant properties may be incorporated into the flange 26, while the viewing lens 20 may contain UV properties as achieved with a particular tint. Alternatively, the flanges 26 may incorporate artwork, lamination, or even a personal fashion statement. The flange 26 may be formed of any material, transparent or solid.

Thus, the present invention has been described herein with reference to a particular embodiments for a particular applications. Those having ordinary skill in the art and access to the present teachings will recognize additional modifications, applications, and embodiments within the scope thereof.

It is therefore intended by the appended claims to cover any and all such applications, modifications and embodiments within the scope of the present invention.

What is claimed is:

1. Eyewear apparatus, comprising:
at least one radically shaped lens with an optical portion having a substantially constant radius of curvature of between 28–19 mm with respect to at least one axis of the lens, and a carrier for the lens at least partially surrounding the lens, the carrier being integral with the lens and extending from the lens at a curvature different than said substantially constant radius of curvature.

2. Eyewear apparatus according to claim 1, wherein:
said at least one radically shaped lens comprises a pair of radically shaped lenses, and said eyewear apparatus includes means for retaining said pair of lenses in a fixed position relative to a wearer.

3. Eyewear apparatus according to claim 2, wherein:
said means for retaining said pair of lenses comprises a frame member supporting said pair of lenses and attached at either end to a strap assembly.

4. Eyewear apparatus according to claim 3, wherein:
said strap assembly includes a pair of elastomeric strap portions spaced from and connected to each other with end portions of one of the strap portions connected at opposite ends to the frame for securing the eyewear in place.

5. Eyewear apparatus according to claim 2, wherein:
each of said pair of lenses includes at least one ventilation passageway extending completely therethrough, allowing air to circulate around both sides of each of the lenses.

6. Eyewear apparatus according to claim 1, wherein:
said at least one radically shaped lens has no discernable peripheral distortion when positioned proximate to an eyeball of normal shape and size.

7. Eyewear apparatus according to claim 1, wherein:
said optical portion of said at least one radically shaped lens is optically correct and free from any prism effect throughout the periphery of the lens and has a 0 power of magnification at all points in a viewing field when constructed of material having an index of refraction of between 1.55 and 1.66.

8. Eyewear apparatus according to claim 1, wherein:
said carrier and lens are seamlessly integral.

9. Eyewear apparatus according to claim 1, wherein:
said carrier is contoured relative to the face of the wearer.

10. Eyewear apparatus according to claim 1, wherein:
said carrier has a continuous change of curvature.

11. Eyewear apparatus according to claim 1, wherein:
the at least one radically shaped lens is formed of transparent material.

12. Eyewear apparatus according to claim 1, wherein:
said carrier extends 360 degrees around said radically shaped lens.

13. Eyewear apparatus according to claim 1, wherein:
the percentage of the lens used for viewing at least 20° in both the vertical and horizontal directions is in the range of 80° to about 94° at a distal portion of the lens.

14. Eyewear apparatus according to claim 13, wherein:
the percentage of the lens used for viewing at least 20° in both the vertical and horizontal directions is in the range of 140° to about 156° at a proximal portion of the lens.

15. Eyewear apparatus according to claim 1, wherein:
said optical portion of said lens has a substantially constant radius of curvature of between 28–19 mm with respect to both axes of said lens.

16. Eyewear apparatus, comprising:
a pair of radically shaped lenses each with optical portions having a substantially constant radius of curvature, and each respective lens of said pair having a respective carrier at least partially surrounding the respective lens, the respective carriers being integral and seamless with the lenses and extending from the lenses at a curvature different than said substantially constant radius of curvature.

17. Eyewear apparatus according to claim 16, wherein:
said optical portions of said pair of lenses are optically correct and free from any prism effect throughout the periphery of the lenses and have a 0 power of magnification at all points in a viewing field when constructed of material having an index of refraction of between 1.55 and 1.66.

18. Eyewear apparatus according to claim 16, wherein:
said substantially constant radius of curvature is between 28–19 mm.

* * * * *